| United States Patent [19] | [11] Patent Number: 4,978,679 |
| Rupprecht et al. | [45] Date of Patent: Dec. 18, 1990 |

[54] 6- AND/OR 7-SUBSTITUTED-1,2,3,4,4A,9B-HEXAHYDRO-8-HYDROXYDIBENZOFURAN-3-OLS AS INHIBITORS OF LEUKOTRIENE BIOSYNTHESIS

[75] Inventors: Kathleen M. Rupprecht, Cranford, N.J.; Joshua S. Boger, Concord, Mass.

[73] Assignee: Merck & Co., Inc., Rahway, N.J.

[21] Appl. No.: 411,787

[22] Filed: Sep. 25, 1989

[51] Int. Cl.$^5$ ..................... A61K 31/34; C07D 307/91
[52] U.S. Cl. .................................. 514/468; 549/457; 549/460
[58] Field of Search ................ 549/460; 514/468

[56] References Cited

U.S. PATENT DOCUMENTS

| 3,317,527 | 5/1967 | Skaletzky et al. | 260/247.7 |
| 3,496,181 | 2/1970 | Skaletzky et al. | 260/268 |
| 3,803,180 | 4/1974 | Berger et al. | 260/346.2 M |
| 3,931,288 | 1/1976 | Berger et al. | 260/473 G |
| 4,857,516 | 8/1989 | Terao et al. | 549/462 |

FOREIGN PATENT DOCUMENTS 0067769 12/1982 European Pat. Off. .
2472569 7/1981 France .

OTHER PUBLICATIONS

K. Brannock et al., J. Org. Chem., 29, 2579, (1964).
W. J. Greenlee et al., Tetrahedron Lett. 24 pp. 4559-4560 (1983).
T. Takahashi et al., Tetrahedron Letters 23, pp. 4361-4364 (1982).
T. Takahashi et al., Tetrahedron Letters 24, pp. 3489-3492 (1983).
A. J. Birch et al., J. Chem. Soc. 1964, pp. 2932-2941.
A. J. Birch and V. H. Powell, Tetrahedron Letters 1970, 3467-3470.
V. H. Powell, Tetrahedron Letters 1970, pp. 3463-3466.

*Primary Examiner*—Mary C. Lee
*Assistant Examiner*—Bernard I. Dentz
*Attorney, Agent, or Firm*—Hesna J. Pfeiffer; William H. Nicholson; Curtis C. Panzer

[57] ABSTRACT

Positions 7- and/or 6-substituted 1,2,3,4,4a,9b-Hexahydro-8-hydroxydibenzofuran-3-ols and analogs of that general structure are described.

These compounds are found to be potent inhibitors of 5-lipoxygenase, an enzyme crucial to the biosynthesis of leukotrienes and useful in the treatment of a variety of inflammatory conditions.

11 Claims, No Drawings

6- AND/OR 7-SUBSTITUTED-1,2,3,4,4A,9B-HEXAHYDRO-8-HYDROXYDIBENZOFURAN-3-OLS AS INHIBITORS OF LEUKOTRIENE BIOSYNTHESIS

BACKGROUND OF THE INVENTION

Compounds of the Formulae I and II:

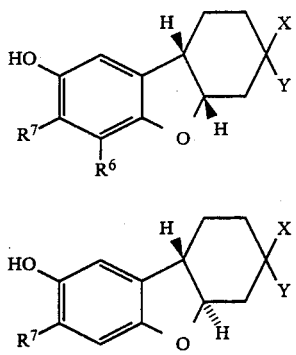

are inhibitors of leukotriene biosynthesis as evidenced by their activity in vitro in the polymorphonuclear leukocyte assay. These compounds inhibit the mammalian 5-lipoxygenase enzyme, thus preventing the metabolism of arachidonic acid to the leukotrienes. Inhibition of 5-lipoxygenase enzyme, therefore diminishes the adverse effects of leukotrienes. The leukotrienes play an important role in inducing allergic reactions, such as: asthma, bronchitis and rhinitis.

There are two groups of leukotrienes derived from a common unstable precursor, Leukotriene $A_4$. The first of these are the peptido-lipid leukotrienes, the most important being leukotrienes $C_4$ and $D_4$. These compounds collectively account for the biologically active materials known as the slow reacting substances of anaphylaxis. They are potent smooth muscle contracting agents, particularly on respiratory smooth muscle, but also on other tissues. In addition they promote mucous production, modulate vascular permeability changes and are potent inflammatory agents in human skin.

The more important compound in the second group of leukotrienes is Leukotriene $B_4$, a dihydroxy fatty acid derived from Leukotriene $A_4$. This compound is a potent chemotactic agent for neutrophils and eosinophils. When injected in vivo, in addition to promoting the accumulation of leukocytes, Leukotriene $B_4$ is also a potent hyperanalgesic agent and can modulate vascular permeability changes through a neutrophil dependent mechanism. Both groups of leukotrienes are formed following oxygenation of arachidonic acid through the action of the 5-lipoxygenase enzyme. See D. Bailey and F. Casey, Ann. Rpts. Med. Chem. 17:203 (1983).

Leukotrienes can also mediate other disease states and these include: psoriasis, atopic dermatitis, gouty arthritis and gall bladder spasms. They also may play a role in cardiovascular disease because Leukotrienes $C_4$ and $D_4$ act as coronary and cerebral arterial vasoconstrictors and these compounds may also have negative ionotropic effects on the myocardium. In addition, the leukotrienes are important mediators of inflammatory diseases through their ability to modulate leukocyte and lymphocyte function. See B. Samuelsson, Science 220:568 (1983).

Recent studies demonstrated that macrophages participate in the development and progression of chronic inflammatory diseases, such as, rheumatoid arthritis. During the progression of inflammatory conditions, there is generally an appearance and/or presence of macrophages and polymorphonuclear leukocytes. Macrophages are known to secrete various products in response to inflammatory stimuli. These oxygenated arachidonic acid products, also known as leukotrienes, have been identified as the critical mediators of various acute inflammatory conditions.

The pharmacological agents such as 5-lipoxygenase inhibitors, which are capable of inhibiting the formation of leukotrienes or agents capable of inhibiting the release of leukotrienes can there by interfere with the function of macrophages or PMN leukocytes. These may also be effective agents in the treatment of a variety of inflammatory conditions, such as: pain, fever, rheumatoid arthritis, emphysema, asthma, allergic disorder, bronchial inflammation, osteoarthritis, acute respiratory distress syndrome, inflammatory bowel disease, spondy citis, lupus, gout, psoriasis, and cardiovascular disorders.

The hexahydrodibenzofuran structural framework has been shown to have anti-inflammatory and analgesic activity. The following patents described the wide variety of uses found for the tetra and hexahydrodibenzofuran structural type.

American Cyanamid has three U.S. Pat. Nos. (3,646,060-S, 3,741,992-S and 3,741,991-S) describing the utility of 4a,9b-dihydro-8,9b-dimethyldibenzofurans as analgesic agents. Ciba-Giegy AG has disclosed in CH 542,838-R, CH-543,500 7- or 8-substituted-alkanoic acid-1,2,3,4-tetrahydrodibenzofurans and thiophenes derivatives as useful hypolipaemic agents. The third utility shown for the dibenzofuran structure type has been demonstrated by Hoffmann-LaRoche in U.S. Pat. Nos. 3,803,180 and 3,931,288 as anti-inflammatory and antirheumatic agents. Parke-Davis & Co. (U.S. Pat. No. 3,159,677) has claimed the 7- and/or 8-substituted-4a-amino-1,2,3,4,9b-tetrahydrodibenzofuran serve as orally and parenterally active CNS-depressants. Merck and Co. has shown in U.S. Pat. No. 4,769,370A that 1,2-dihalo or dialkyl-8-oxo-5a-substituted-tetrahydrodibenzofuran-3-ylalkanoic acids and alkanimidamides are useful for the treatment of injury to the brain or spinal cord. Riom Labs has discovered the 4a-4-phenylhydroxyethylpiperazinylmethyl-1,2,3,4,4a,9b-hexahydrodibenzofuran-4-one or 4-ol derivatives described in EP 67-769 are antibronchoconstrictors. Nippon Soda in J6 0016-980A has shown 1,2,3,4,4a,9b-hexahydro-9-{2-hydroxy-3-(1-methylethylamino)propoxy} dibenzofuran derivatives to have beta-blocking activity. Hoechst Roussel Pharmaceutical in U.S. Pat. No. 3,646,060-S and Upjohn Co. in Neth. 6,415,270 describe the use of 1,2,3,4,4a,9b-hexahydro-4a-aminoalkyldibenzofurans as analgesics, anticonvulsants and antidepressants.

The structures described within this application have a novel substitution pattern which is felt to enhance the binding to the 5-lipoxygenase enzyme and in turn better inhibit the production of leukotrienes, thereby enhance the anti-inflammatory activity.

DETAILED DESCRIPTION OF THE INVENTION

A Scope of the Invention

This invention relates to novel compounds of the Formulae I and II:

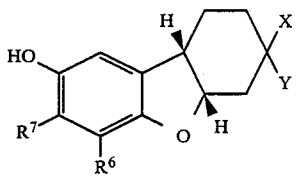

I

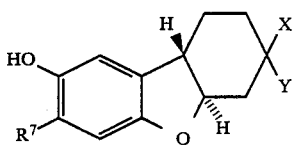

II wherein:

$R^6$ is:
  hydrogen, when $R^7$ is not hydrogen except when $R^6$ and $R^7$ are joined to form a ring, wherein the ring is defined as a 6-membered saturated, unsaturated or aromatic ring containing a carbon framework,
  $(C_1-C_6)$-alkyl,
  $(C_1-C_6)$-branched alkyl, or
  $(C_2-C_6)$-alkenyl; and $R^7$ is:
  hydrogen,
  $(C_1-C_6)$-alkyl,
  $(C_1-C_6)$-branched alkyl, or
  $(C_2-C_6)$-alkenyl; and X and Y together are a keto group, or X and Y are different and are independently H, OH, $(C_1-C_6)$-alkyl, or phenyl, except that if X or Y is $(C_1-C_6)$-alkyl, then Y or X cannot be phenyl, or pharmaceutically acceptable salts thereof.

The preferred embodiment of the invention for compounds of Formula I are:

$R^6$ is:
  hydrogen, when $R^7$ is not hydrogen,
  1-prop-2-enyl, when $R^7$ is hydrogen,
  n-propyl, when $R^7$ is hydrogen, or $R^6$ and $R^7$ are joined to form a phenyl ring; and $R^7$ is:
  hydrogen,
  1-prop-2-enyl, when $R^6$ is hydrogen, or
  n-propyl, when $R^6$ is hydrogen; and X is:
  hydrogen,
  hydroxyl,
  phenyl, or
  n-butyl; and Y is:
  hydrogen,
  hydroxyl, or X and Y together are a keto group,
or pharmaceutically acceptable salts thereof.

The preferred embodiment of the invention for compounds of Formula II are:

$R^6$ is: hydrogen; and
$R^7$ is:
  1-prop-2-enyl, or
  n-propyl; and

X and Y together are a keto group
or pharmaceutically acceptable salts thereof.

The most preferred embodiment of the invention for compounds of the formulae I and II are:

1. (4aS*, 9bS*)-1,2,3,4,4a,9b-hexahydro-8-hydroxy-6-propylidibenzofuran-3-one
2. (4aS*, 9bS*)-1,2,3,4,4a,9b-hexahydro-8-hydroxy-7-propyldibenzofuran-3-one
3. (4aR*, 9bS*)-1,2,3,4,4a,9b-hexahydro-8-hydroxy-7-prop-2-enyldibenzofuran-3-one
4. (4aR*, 9bS*)-1,2,3,4,4a,9b-hexahydro-8-hydroxy-7-propyldibenzofuran-3-one
5. (4aS*, 9bS*)-1,2,3,4,4a,9b-hexahydro-8-hydroxynapthobenzofuran-3-one
6. (4aS*, 9bS*, 3R*)-3,8-dihydroxy-1,2,3,4,4a,9b-hexahydro-3-phenyl-7-propyldibenzofuran
7. (4aS*, 9bS*, 3R*)-3,8-dihydroxy-1,2,3,4,4a,9b-hexahydro-3-n-butyl-7-propyldibenzofuran
8. (4aS*, 9bS*, 3R*)-3,8-dihydroxy-1,2,3,4,4a,9b-hexahydro-7-propyldibenzofuran
9. (4aS*, 9bS*, 3S*)-3,8-dihydroxy-1,2,3,4,4a,9b-hexahydro-7-prop-2-enyldibenzofuran
10. (4aS*, 9bS*, 3S*)-3,8-dihydroxy-1,2,3,4,4a,9b-hexahydro-7-propyldibenzofuran
11. (4aS*, 9bS*, 3R*)-1,2,3,4,4a,9b-hexahydro-8-hydroxy-3-phenyl-7-propyldibenzofuran
12. (4aR*, 9bS*, 3S*)-3,8-dihydroxy-1,2,3,4,4a,9b-hexahydro-7-prop-2-enyldibenzofuran
13. (4aR*, 9bS*, 3S*)-3,8-dihydroxy-1,2,3,4,4a,9b-hexahydro-3-phenyl-7-prop-2-enyldibenzofuran
14. (4aR*, 9bS*, 3R*)-3-cyano-3,8-dihydroxy-1,2,3,4,4a,9b-hexahydrodibenzofuran The compounds of the present invention are conveniently prepared following the procedures described in Schemes I to IV and more explicitly in the specific Examples thereafter.

The dibenzofuran skeleton is prepared as shown in Scheme I using a Diels-Alder reaction between a 2-substituted-1,4-benzoquinone and 1-methoxy-1,3-cyclohexadiene which results in the preparation of the two isomeric tetrahydronaphthalenediones. Acid catalyzed rearrangement of these isomeric tetrahydronaphthalenediones gives the corresponding 6-and 7- substituted dibenzofurans, compounds A and B.

SCHEME I

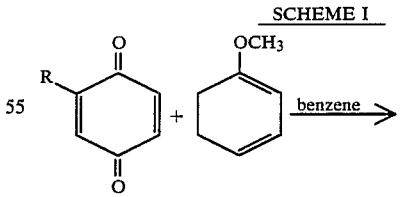

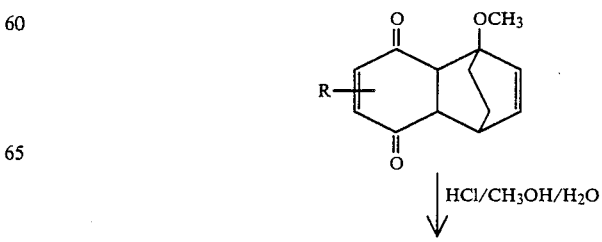

-continued
SCHEME I

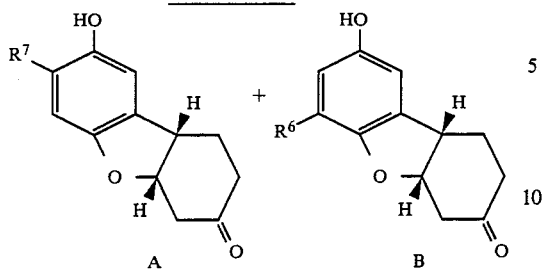

Wherein R is either R[6] or R[7] and R[6] and R[7] are as defined in the specifications.

Scheme II describeds the synthesis of the napthobenzofuran-3-one, which is prepared by using a Diels-Alder reaction of 1,4-napthoquinone with 1-methoxy-1,3-cyclohexadiene followed by an acid-mediated rearrangement to give compound C.

SCHEME II

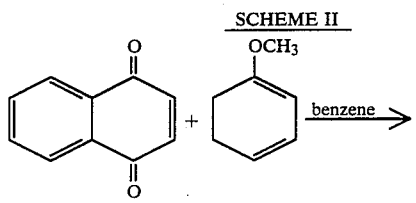

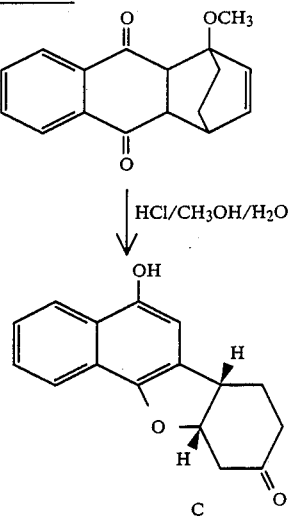

The preparation of dibenzofuran A was accomplished using the reactions described in Scheme III, the 8-hydroxy-1,2,3,4-tetrahydrodibenzofuran-3-one, where R[6] and R[7] are hydrogen, is reduced with triethylsilyl hydride to give the isomeric alcohols of the cis-fused dibenzofuran. Alkylation of the 8-hydroxyl group with allyl bromide and $K_2CO_3$, crystallization of the 3S-isomer allowed for the separation of diastereomers. A Claisen rearrangement of the allyl ether gave the (4aS*, 9bS*, 3S*)-1,2,3,4,4a,9b-hexahydro-8-hydroxy-6-(1-prop-2-enyl)dibenzofuran-3-ol, compound D. Reduction of the allyl group by catalytic hydrogenation gave compound E, (4aS*, 9bS*, 3S*)-1,2,3,4,4a,9b-hexahydro-8-hydroxy-6-propyldibenzo-furan-3-ol.

SCHEME III

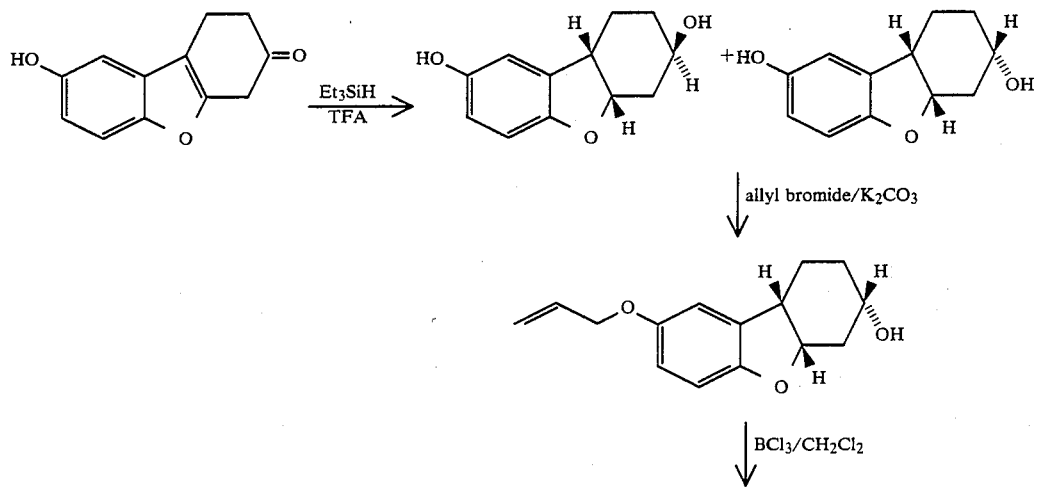

-continued
SCHEME III

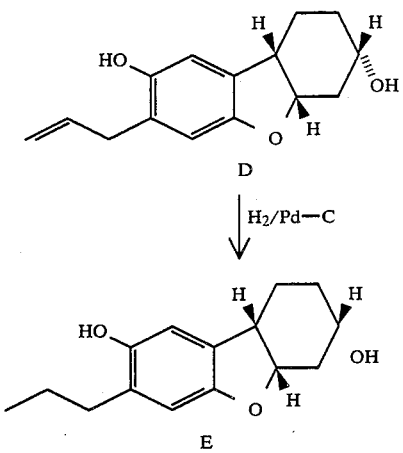

The ketone of compound A, (4aS*, 9bS*)-1,2,3,4,4a,9b-hexahydro-8-hydroxy-7-propylidibenzofuran-3-one was reduced as shown in Scheme IV using the two procedures shown, triethylsilylhydride and trifluoroacetic acid, as well as, sodium borohydride. The silylhydride reduction resulted in the preparation of the R-alcohol where as the sodium borohydride resulted in the S-alcohol, with delivery of the hydride from the top face the dibenzofuran-3-one system.

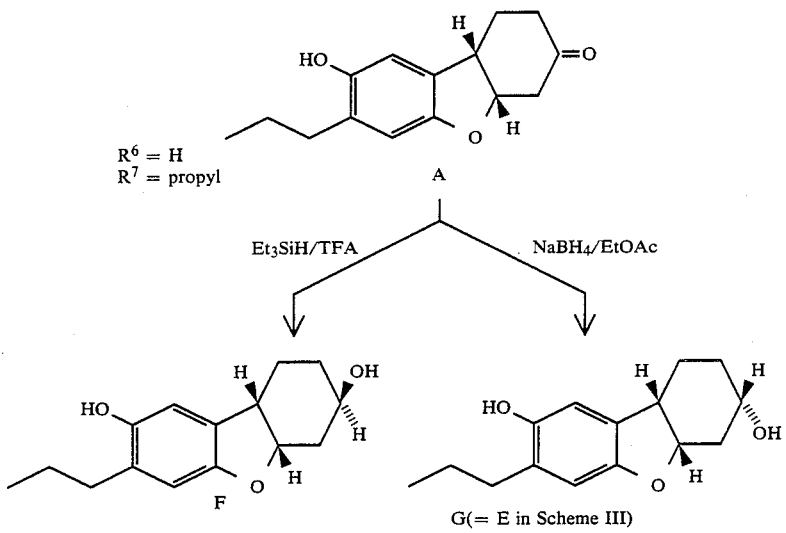

Scheme V describes the reductive alkylation of compound A with phenylmagnesium bromide and n-butyl lithium to yield in each case a single diastereomer, compounds H and I, respectively. The phenyl substituted alcohol was reduced with retention of configuration using hydrogen and palladium on carbon to give the methine compound, compound J.

SCHEME V

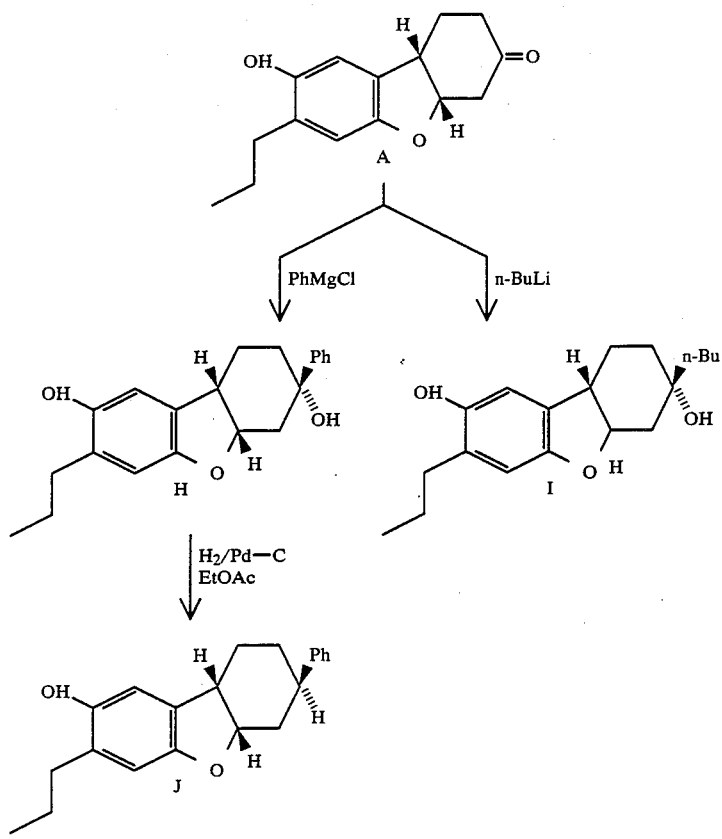

The trans dibenzofuran shown in Formula II is prepared using the chemistry described by Skatelzky in Scheme VI (Skaletzky, L.L. U.S. Pat. Nos. 3,317,527, 1967; Skaletzky, L.L. 3,337,563, 1967; Skaletzky, L.L. 3,496,181, 1968) to synthesize the 5-(prop-2-enyloxy)-3-substituted-2,3-dihydrobenzofuran-2-ol, compound K, which reacts as an aldehyde equivalent with a Wittig reagent to give the 2,3-disubstituted-2,3-dihydrobenzofuran, compound L, which is elaborated further to generate the third ring.

The methoxymethyl ether is hydrolyzed to hydroxyl compound, compound M, and subsequent halogenation to the chloride, compound N. A DIBAL-H reduction of compound N gives the aldehyde, compound O, which undergoes a 1,2 addition to the aldehyde with trimethylsilylcyanide, compound P. The deprotection of the silyl ether with n-Bu$_4$NF and subsequent protection with ethyl vinyl ether, a more base stable protecting group, gives compound O. The cyclization of compound O is accomplished using sodium hexamethyldisilazide in THF at 60° C. The cyclized product, compound R, is deprotected by hydrogenolysis to give the cyanohydrin, compound S. The cyanohydrin is subsequently converted to ketone T by heating in dimethylsulfoxide under vacuum at 45° C.

SCHEME VI*

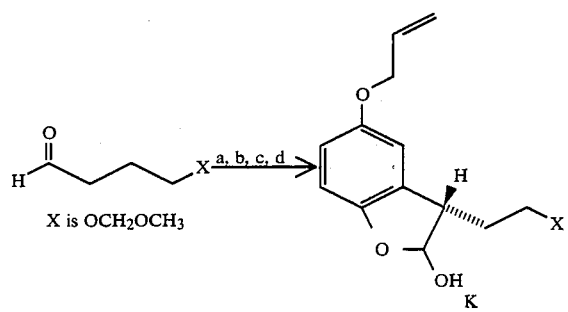

-continued

SCHEME VI*

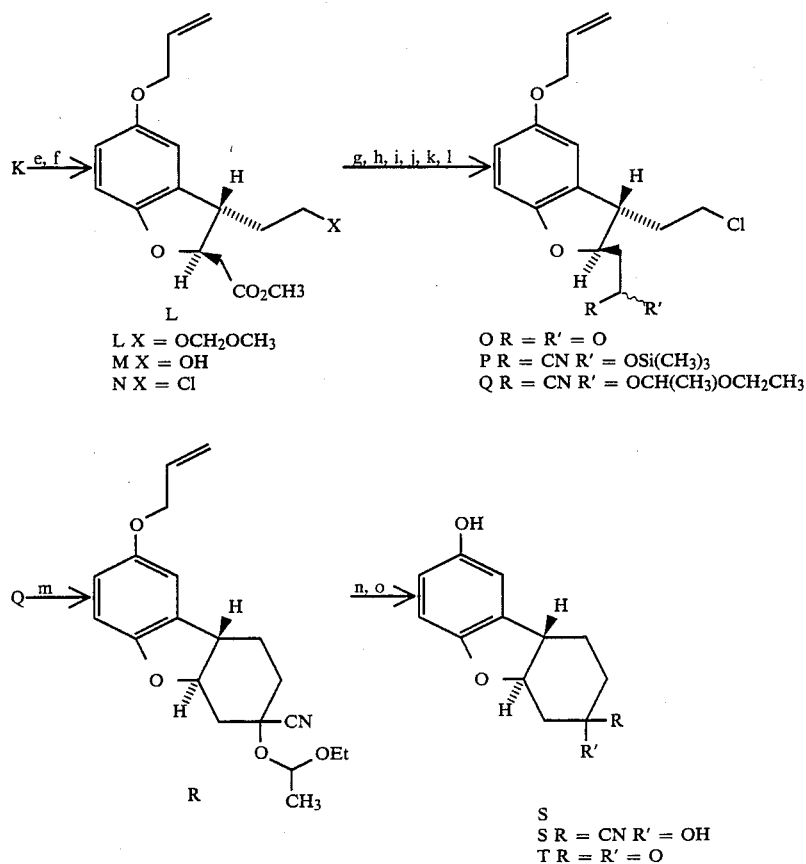

L X = OCH2OCH3
M X = OH
N X = Cl

O R = R' = O
P R = CN R' = OSi(CH3)3
Q R = CN R' = OCH(CH3)OCH2CH3

S R = CN R' = OH
T R = R' = O

The key for the reactions shown in Scheme VI is on the following page.
*a piperidine, p-TsOH, benzene, reflux;
 b benzoquinone;
 c KOt-Bu, allyl bromide, THF;
 d H2O, silica gel;
 e Ph3PCHCO2H, THF;
 f piperidine, CH3OH, reflux;
 g BF3, CH3OH;
 h Ph3P, CCl4, CH3CN;
 i DIBAL—H, toluene, −78° C.;
 j (CH3)3SiCN, KCN, 25° C.;
 k Bu4NF, CF3CO2H, THF;
 l CH2CHOCH2CH3, CF3CO2H, THF, 0° C.;
 m NaN[Si(CH3)3]2, THF, 60° C.;
 n 10% Pd/C, p-TsOH, CH3OH—C6H6, 70° C.;
 o (CH3)2SO, 45° C., 100 mm vacuum.

Scheme VII

Scheme VII illustrates the Claisen rearrangement of compound R using BCl3 strong acid and obtaining the desired 8-hydroxyl-7-(2-propenyl)dibenzofuran but, also effects the deprotection of the acid labile protecting group to give the 3-hydroxyl compounds which underwent the elimination of HCN to give the ketone U.

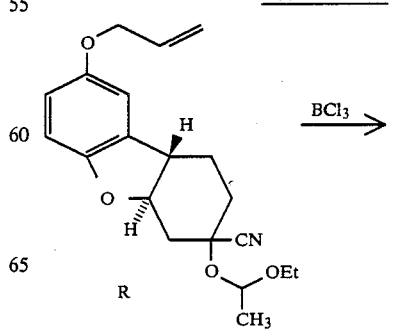

-continued
Scheme VII

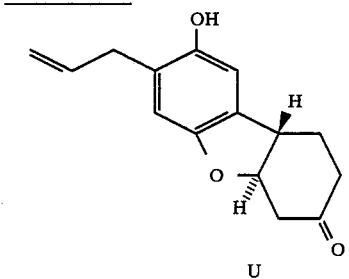

U

B Utility of the Subject Compounds of the Invention

This invention also relates to a method of treating inflammation in patients in need of such treatment. Generally, an effective non-toxic amount of a compound of Formula (I) or a pharmaceutical composition thereof, particularly an especially preferred compound, is administered to the patient as the active constituent.

To demonstrate the utility of the present invention, representative novel compounds of formula I were evaluated for their ability to inhibit the production of leukotriene $B_4$ ($LTB_4$) in isolated rat and human polymorphonuclear leukocytes (PMN). Other compounds known to inhibit leukotriene biosynthesis have been shown to have activity in this assay, and thus the assay is of value in predicting in vivo activity. Thereby useful in determining the dosage and route of administration.

For the treatment of inflammation, arthritis conditions, psoriasis, asthma, or other diseases mediated by prostaglandins, a compound of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intravascular injection or infusion techniques. In addition to the treatment of warmblooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lonzenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient inadmixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelation or acacia, and lubricating agents, for example magnesium stearate, stearic acid or talc. The tablets may be uncoated or they may be coated by known techniques to delay distintegration and absorption in the gastrointestinal tract and thereby provide a sustained action over a longer period. For example, a time delay material such as glyceryl monosterate or glyceryl disterate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut (arachis) oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents may be anaturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial ester derived from fatty acids and hexitol anhydrides, for example, polyoxyethylene sorbitan monooleate. The said aqueous suspensions may also contain one or more preservatives, for example, ethyl, or n-propyl p-hydroxybenzoate.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. These compositions may be preserved by the addition of an antioxidant such as ascorbic acid.

Dispersible powders and granules are suitable for the preparation of an aqueous suspension by mixing them with water. They provide the active ingredient in admixture with a dispersing or wetting agent, a suspending agent and one or more preservatives. Suitable dispersing or wetting agents and suspending agents are exemplified by those already mentioned above.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally occurring gums, for example, gum acacia or gum tragacanth, naturally-occurring phosphatides, for example, soy bean, lecithin, and esters or partial ester derived from fatty acids and hexitol anhydrides, for example, sorbitan mono-oleate, and condensation products of the said partial esters with enthylene oxide, for example, polyoxyethylene sorbitan monooleate.

An ointment containing the pharmaceutical compositions of the present invention may be prepared, among other methods known in the art, by combining the active ingredient with a medium consisting of a glycol, a lower alkanol, and water; a gelling agent; and optionally an adjuvant such as diisopropyl adipate, diethyl sebacate, ethyl caproate and ethyl laurate. Suitable glycols include propylene glycol, butylene glycol, polyethylene glycol and the like. Generally, a carboxyvinyl polymer preneutralized with an organic amine such as diisopropyl amine and triethylamine, or a cellulose, e.g., hydroxyethyl cellulose, methyl cellulose, carboxymethyl cellulose, hydroxypropyl cellulose, is used as the gelling agent.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

The preferred route of administration is an oral route. In oral administration the drug can be employed in any of the usual dosage forms such as tablets, capsules, solutions, suspensions or powders, either in a contemporanious delivery or sustained release form. Any number of the usual excipients or tableting aids can likewise be included.

Dosage levels of the order to 0.2 mg to 140 mg per kilogram of body weight per day are useful in the treatment of the above-indicated condition (10 mg to 7 gms per patient per day). For example, inflammation is effectively treated by the administration from about 0.5 to 50 mg of the compound per kilogram of body weight per day (25 mg to 5 gms per patient per day).

The amount of active ingredient that may be combined with the carrier materials to produce a single dosage will vary depending upon the host treated and the particular mode of administration. Dosage unit forms will generally contain from about 25 mg to about 1 g of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Representative compounds of Formula I have been tested using the following two assays described below:

A. Preparation of Human PMN. Human blood is obtained by antecubital venepuncture from consenting volunteers who denied having taken medication within the previous 7 days. The blood is immediately added to 10% (v/v) trisodium citrate (0.13M) or 5% (v/v) sodium heparin (1000 IU/mL). PMNs are isolated from anticoagulated blood by dextran sedimentation and centrifugation through Ficoll-Hypaque (specific gravity 1.077), essentially as described by Boyum. (Boyum, A., Scand. J. Clin. Lab. Invest. 1968, 21 (Supp 97), 77). Contaminating erthrocytes are removed by lysis following exposure to ammonium chloride (0.16M) in Tris buffer (pH 7.65), and the PMNs resuspended at $5 \times 10^5$ cells/mL in HEPES (15 mM) buffered Hanks balanced salt solution containing $Ca^{2+}$ (1.4 mM) and $Mg^{2+}$ (0.7 mM), pH 7.4. Viability is assessed by Trypan blue exclusion and is typically greater than 98%.

B. Rat Peritoneal Polymorphonuclear leukocytes (PMN). Male Sprague-Dawley rats were purchased from Taconic Farms, Germantown, NY. The animals were maintained on standard pellet diet and water ad lib. Elicited PMN were prepared from peritoneal exudates as follows: 8 ml of 12% sodium caseinate was injected intraperitoneally into male rats. After 18–20 hours, the rats were killed with $CO_2$ and the peritoneal cavities were lavaged with Eagle's MEM (pH 7.7) without $NaHCO_3$ but containing Earle's salts, L-glutamine, and 30 mM HEPES. The PMN were isolated by centrifugation, washed with MEM, filtered through lens paper to remove clumps, and adjusted to a concentration of $1 \times 10^7$ cells/ml.

The following examples illustrate the preparation of the compounds of the formula (I) and as such are not to be considered as limiting the invention set forth in the claims appended hereto.

EXAMPLE 1

(4aS*,9bS*)-1,2,3,4,4a,9b-Hexahydro-8-hydroxy-7-methyldibenzofuran-3-one

A solution of 0.57 g (5.0 mmol) of 2-methyl-1,4-benzoquinone and 1.10 g (10.0 mmol) of 1-methoxy-1,3-cyclohexadiene in 10 mL of benzene was heated at reflux for 2 h. The solution was concentrated in vacuo and the residue dried under high vacuum to afford a pale yellow oil. This material was dissolved in 15 mL of methanol and to that solution was added 1 mL of 2.0M HCl. The solution was stirred at room temperature for 6 hours, then was concentrated to about 5 mL volume. This was partitioned between ethyl acetate and water and the aqueous layer was washed with two portions of ethyl acetate. The organic extracts were sequentially washed with water and NaCl solution, combined, dried over magnesium sulfate, and concentrated. The residue was crystallized from ether-hexane to afford 0.452 g white crystals, 41%.

$^1$H NMR (300 MHz, $CD_3CN$, ppm): 1.8–2.0 (m, 2H), 2.1–2.3 (m, 2H), 2.42 (s, 3H), 2.66 (AB, dd, J=16.5, 4.0 Hz, 1H), 2.81 (AB, dd, J=16.5, 4.0 Hz, 1H), 3.71 (m, 1H), 5.18 (dt, J=9.5, 4.0 Hz, 1H), 6.49 (s, b, 1H), 6.55 (s, 1H), 6.70 (s, 1H);

M.S. (FAB, M+H): 219.

EXAMPLE 2

(4aS*,9bS*)-1,2,3,4,4a,9b-Hexahydro-8-hydroxy-7-propyldibenzofuran-3-one

A solution of 1.08 g (7.2 mmol) of 2-propyl-1,4-benzoquinone and 2.20 g (20.0 mmol) of 1-methoxy-1,3-cyclohexadiene in 20 mL of benzene was heated at reflux for 2 h. The solution was concentrated in vacuo and the residue dried under high vacuum to afford a pale yellow oil. This material was dissolved in 20 mL of methanol and to that solution was added 1 mL of 2.0M HCl. The solution was stirred at room temperature for 6 hours, then was concentrated to about 5 mL volume. This was partitioned between ethyl acetate and water and the aqueous layer was washed with two portions of ethyl acetate. The organic extracts were sequentially washed with water and NaCl solution, combined, dried over magnesium sulfate, and concentrated. The residue was crystallized from ether-hexane to afford 0.764 g white crystals, 43%.

$^1$H NMR (300 MHz, $CD_3CN$, ppm): 0.05 (t, J=7 Hz, 3H), 1.60 (m, 2H), 2.50 (t, J=7 Hz, 2H), 1.8–2.0 (m, 2H), 2.1–2.3 (m, 2H), 2.66 (AB, dd, J=16.5, 4.0 Hz, 1H), 2.81 (AB, dd, J=16.5, 4.0 Hz, 1H), 3.71 (m, 1H), 5.18 (dt, J=9.5, 4.0 Hz, 1H), 6.49 (s, b, 1H), 6.55 (s, 1H), 6.70 (s, 1H);

M.S. (FAB, M+H): 247.

EXAMPLE 3

(4aS*,9bS*)-1,2,3,4,4a,9b-Hexahydro-8-hydroxy-6-propyldibenzofuran-3-one

The above filtrate was purified by flash chromatography on a 4 mm column using 30% ethyl acetate-hexane eluant to afford 0.838 g of the 5-propyl isomer as a white solid, 47%;

$^1$H NMR (300 MHz, CD$_3$CN, ppm): 0.05 (t, J=7 Hz, 3H), 1.60 (m, 2H), 2.50 (t, J=7 Hz, 2H), 1.8–2.0 (m, 2H), 2.1–2.3 (m, 2H), 2.66 (AB, dd, J=16.5, 4.0 Hz, 1H), 2.81 (AB, dd, J=16.5, 4.0 Hz, 1H), 3.71 (m, 1H), 5.18 (dt, J=9.5, 4.0 Hz, 1H), 6.49 (s, b, 1H), 6.6 (d, J=4 Hz, 1H), 6.74 (d, J=4 Hz, 1H);

M.S. (FAB, M+H): 247.

EXAMPLE 4

(6bS*,10aS*)-[6bH]-7,8,10,10a-Tetrahydro-5-hydroxybenzo[b]naphtho-(2,1-d)furan-9-one A solution of 1.58 g (10.0 mmol) of 1,4-naphthoquinone and 2.20 g (20.0 mmol) of 1-methoxy-1,3-cylcohexadiene in 20 mL of benzene was heated at reflux for 2 h. The solution was concentrated in vacuo and the residue dried under high vacuum to afford 2.70 g of a brown solid that began darkening upon exposure to air. This material was immediatelyt dissolved in 20 mL of methanol and to that solution was added 1 mL of 2.0M HCl. The solution was stirred at room temperature for 6 hours, then was concentrated to about 5 mL volume. This was partitioned between ethyl acetate and water and the aqueous layer was washed with two portions of ethyl acetate. The organic extracts were sequentially washed with water and NaCl solution, combined, dried over magnesium sulfate, and concentrated. The residue was crystallized from ether-hexane to afford 2.05 g of pale tan crystals, 81%.

$^1$H NMR (300 MHz, CD$_3$CN, ppm): 0.95 (t, J=7 Hz, 3H), 1.60 (m, 2H), 2.50 (t, J=7 Hz, 2H), 1.8–2.0 (m, 2H), 2.1–2.3 (m, 2H), ), 2.66 (AB, dd, J=16.5, 4.0 Hz, 1H), 2.81 (AB, dd, J=16.5, 4.0 Hz, 1H), 3.71 (m, 1H), 5.18 (dt, J=9.5, 4.0 Hz, 1H), 6.49 (s, b, 1H), 6.6 (d, J=4 Hz, 1H), 6.74 (d, J=4 Hz, 1H), 7.x (m, 4H);

M.S. (FAB, M+H): 255.

EXAMPLE 5

(4aS*,9bS*,3S*)-3,8-Dihydroxy-1,2,3,4,4a,9b-hexahydro-7-(2-propenyl)dibenzofuran

Step A:
(4aS*,9bS*,3S*)-3,8-Dihydroxy-1,2,3,4,4a,9b-hexahydrodibenzofuran

A solution of 2.02 g (10 mmole) of (4aS*,9bS*)-3,8-hydroxy-1,2,3,4-tetrahydrodibenzofuran-3-one in 20 mL of trifluoroacetic acid and 5 mL of triethylsilane was stirred at room temperature for 24 h. Then 10 mL of methanol was added and the solution was stirred for an additional 30 min. The solution was concentrated and the remaining acid was removed by azeotropic distillation with toluene. The residue was crystallized from ethyl acetate-hexane to afford 1.58 g (77%) of white prisms that represented a 4:1 mixture of C3-diastereomers.

$^1$H NMR (300 MHz, CD$_3$CN, ppm): 1.25 (m, 1.4H), 1.42 (ddd, J=13, 9, 8.5 Hz, 0.8H), 1.70 (m, 2.2H), 2.06 (m, 2H), 2.69 (d, J=5.5 Hz, 0.8H, —OH), 2.78 (d, J=4.5 Hz, 0.2H, —OH), 2.99 (dt, J=9, 6.5 Hz, 0.2H), 3.30 (dt, J=6.5, 5 Hz, 0.8H), 3.57 (ddt, J=9, 5.5, 4.5 Hz 0.8H), 3.74 (dtt, J=10, 5.5, 4.5 Hz, 0.2H) 4.74 (ddt, J=8.5, 6.5 Hz, 0.80H), 4.84 (dt, J=6.5, 4 Hz, 0.20H), 6.42 (sb, 1H), 6.52 (m, 1 Hz, 1H), 6.56 (m, 1H), 6.60 (m, 0.20H), 6.64 (m, 1H).

Step B:
(4aS*,9bS*,3S*)-3-Hydroxy-1,2,3,4,4a,9b-hexahydro-8-(2-propenyloxy)dibenzofuran A mixture of 1.40 g (6.86 mmol) of the product of Example 5, Step A, 2.5 g (mmol) of K$_2$CO$_3$ and 2.4 g (mmol) of allyl bromide in 10 mL of dry acetone was heated under reflux for 18 h. The solution was partitioned between ether and water and the aqueous layer was extracted with ether. The organic extractes were washed with saturated Na$_2$CO$_3$ solution and brine, and the combined extracts were dried over MgSO$_4$ and concentrated to an oil. This crystallized from ethyl acetate-hexane to afford 1.03 g of white prisms that was a single C3-diastereomer (75% based on a 4:1 mixture of starting epimers).

$^1$H NMR (300 MHz, CD$_3$CN, ppm): 1.25 (m, 1H), 1.42 (ddd, J=13, 9, 8.5 Hz, 1H), 1.70 (m, 2H), 2.06 (m, 2H), 2.69 (d, J=5.5 Hz, 1H, —OH), 3.30 (dt, J=6.5, 5 Hz, 1H), 3.57 (ddt, J=9, 5.5, 4.5 Hz, 1H), 4.45 (dt, J=5.5, 1.5, 2H), 4.74 (ddt, J=8.5, 6.5 Hz, 1H), 5.26 (dq, J=10.5, 1.5 Hz, 1H), 5.38 (dq, J-17, 1.5 Hz, 1H), 6.03 (ddt, J-17, 10.5, 5.5 Hz, 1H) 6.52 (m, 1H), 6.56 (m, 1H), 6.64 (m, 1H).

M.S. (FAB M+H): 249.

Step C:
(4aS*,9bS*,3S*)-3,8-Dihydroxy-1,2,3,4,4a,9b-hexahydro-7-(2-propenyl)dibenzofuran A solution of 1.0 g (4 mmol) of the product of Example 5, Step B in 20 mL of CH$_2$Cl$_2$ was cooled to 0° C. under nitrogen. Then 4.0 mL of a 1M BCl$_3$ solution in CH$_2$Cl$_2$ was added dropwise and the solution was stirred at room temperature for 30 min. The reaction was quenched by addition of 10 mL of saturated NaHCO$_3$ solution and the mixture was partitioned between ether and water. The organic extract was washed with saturated NaHCO$_3$ solution and brine, dried over MgSO$_4$, and concentrated. The oily residue was crystallized from ethyl acetate-hexane to afford 0.786 g (79%) of white prisms.

$^1$H NMR (300 MHz, CD$_3$CN, ppm): 1.25 (m, 1H), 1.42 (ddd, J=13, 9, 8.5 Hz, 1H), 1.70 (m, 2H), 2.06 (m, 2H), 2.69 (d, J=5.5 Hz, 1H, —OH), 3.30 (dt, J=6.5, 5 Hz, 1H), 3.38 (m, 2H), 3.57 (ddt, J=9, 5.5, 4.5 Hz, 1H), 4.74 (ddt, J=8.5, 6.5 Hz, 1H), 5.20 (m, 3H), 6.52 (m, 1H), 6.56 (m, 1H), 6.64 (m, 1H).

M.S. (FAB M+H): 249.

EXAMPLE 6

(4aS*,9bS*,3S*)-3,8-Dihydroxy-1,2,3,4,4a,9b-hexahydro-7-propyldibenzofuran

A solution of 0.125 g (0.59 mmol) of the product of Example 5, Step C and 50 mg of 5% Pd/C in 10 mL of ethyl acetate was shaken under 40 psi H$_2$ for 1 h. The solution was filtered through Celite and the filtrate concentrated to a colorless oil that crystallized from ethyl acetate-hexane to afford 0.120 g (98%) of white prisms.

$^1$H NMR (300 MHz, CD$_3$CN, ppm): 0.95 (t, J=7 Hz, 3H), 1.25 (m, 1H), 1.4–1.8 (m, 4H), 2.06 (m, 2H), 2.54 (t, J=7 Hz, 2H), 2.69 (d, J=5.5 Hz, 1H, —OH), 3.30 (dt, J=6.5, 5 Hz, 1H), 3.57 (ddt, J=9, 5.5, 4.5 Hz), 4.74 (ddt, J=8.5, 6.5 Hz, 1H), 6.47 (sb, 1H), 6.52 (AB, ddd, J=8.5, 2.5, 1 Hz, 1H), 6.56 (AB, dd, J=8.5, 0.5 Hz, 1H), 6.64 (ddd, J=2.5, 1, 0.5 Hz, 1H);
M.S. (FAB M+H): 249.

EXAMPLE 7 (ALTERNATE ROUTE)

(4aS*,9bS*,3S*)-3,8-Dihydroxy-1,2,3,4,4a,9b-hexahydro-7-propyldibenzofuran

A solution of 0.246 g (1.0 mmole) of the product of Example 2, Step A in 10 mL of ethyl acetate was cooled to 0° C. in an ice bath. To this was added 0.035 g (1.0 mmole) of NaBH4 and the solution was stirred at 0° C. for 5 h. Excess hydride was decomposed by addition of 1 mL of saturated NH4Cl solution and the mixture was partitioned between ethyl acetate and 0.02M HCl. The aqueous layer was washed with two portions of ethyl acetate and the organic extracts were washed sequentially with saturated NaCl solution, combined, and dried over magnesium sulfate. The solution was filtered and concentrated, and the residue crystallized from ethyl acetate-hexane to afford 0.178 g (72%) of colorless prisms.

$^1$H NMR (300 MHz, CD$_3$CN, ppm): 0.95 (t, J=7 Hz, 3H), 1.25 (m, 1H), 1.4–1.8 (m, 4H), 2.06 (m, 2H), 2.54 (t, J=7 Hz, 2H), 2.69 (d, J=5.5 Hz, 1H, —OH), 3.30 (dt, J=6.5, 5 Hz, 1H), 3.57 (ddt, J=9, 5.5, 4.5 Hz), 4.74 (ddt, J=8.5, 6.5 Hz, 1H), 6.47 (sb, 1H), 6.52 (AB, ddd, J=8.5, 2.5, 1 Hz, 1H), 6.56 (AB, dd, J=8.5, 0.5 Hz, 1H), 6.64 (ddd, J=2.5, 1, 0.5 Hz, 1H);
M.S. (FAB M+H): 249.

EXAMPLE 8

(4aS*,9bS*,3R*)-3,8-Dihydroxy-1,2,3,4,4a,9b-hexahydro-7-propyldibenzofuran

A solution of 0.246 g (1.0 mmole) of the product of Example 2, Step A in 2 mL of trifluoroacetic acid was cooled to 0° C. To this was added 0.5 mL (3.2 mmole) of triethylsilane and the solution was stirred at 0° C. for 1 h. The solution was concentrated and the residual trifluoroacetic acid was removed by azeotropic distillation with toluene. The residue was crystallized from ether to afford 0.107 g (43%) of white prisms.

$^1$H NMR (300 MHz, CD$_3$CN, ppm): 0.91 (t, J=7, 3H), 1.28 (m, 2H), 1.64 (m, 4H), 2.23 (AB, dddd, J=14, 4, 3.5, 2 Hz, 1H), 2.54 (t, J=7 Hz, 2H), 2.78 (d, J=4.5, 1H, —OH), 2.99 (dt, J=9, 6.5 Hz, 1H), 3.74 (dtt, J=10, 5.5, 4.5 Hz, 1H), 4.84 (dt, J=6.5, 4 Hz, 1H), 6.39 (sb, 1H), 6.50 (AB, dd, J=8, 2.1 Hz, 1H), 6.56 (AB, D, J=8 Hz, 1H), 6.60 (d, J=2.5 Hz, 1H);
M.S. (FAB M+H): 249.

EXAMPLE 9

(4aS*,9bS*,3S*)-3,8-Dihydroxy-1,2,3,4,4a,9b-hexahydro-3-phenyl-7-propyldibenzofuran A solution of 0.630 g (2.5 mmole) of the product of Example 2, Step A in 10 mL THF was cooled to −78° C. in a dry ice-acetone bath. Then 4 mL of a 2M solution of phenyl magnesium chloride in tetrahydrofuran was added dropwise over 15 min and the mixture was stirred, first at −78° C. for 1 h, then at 0° C. for 30 min. The reaction was quenched by addition of 10 mL of saturated NH4Cl solution and the mixture was partitioned between ethyl acetate and saturated NH4Cl solution. The aqueous layer was washed with ethyl acetate and the organic extracts were washed sequentially with saturated NH4Cl and saturated NaCl solution, dried over magnesium sulfate, and concentrated. The residue was purified by flash chromatography (3 cm column) using 25% ethyl acetate-hexane eluant to afford 0.385 g (48%) of colorless needles.

$^1$H NMR (300 MHz, CD$_3$CN, ppm): 0.91 (t, J=7 Hz, 3H), 1.5–1.75 (m, 4H), 1.86 (m, 1H), 2.10 (m, 1H), 2.28 (d, J=3.5 Hz, 2H), 2.54 (t, J=6 Hz, 2H), 3.09 (ddd, J=10, 7, 6 Hz, 1H), 4.68 (ddt, J=6, 3.5, 1 Hz, 1H), 6.46 (sb, 1H), 6.56 (AB, dd, J=8.5, 2.5 Hz, 1H), 6.65 (AB, d, J=8.5 Hz, 1H), 6.74 (d, J=2.5 Hz, 1H), 7.25 (m, 1H), 7.36 (m, 2H), 7.54 (m, 2H);
M.S. (FAB, M+H) 325.

EXAMPLE 10

(4aS*,9bS*,3S*)-1,2,3,4,4a,9b-hexahydro-8-hydroxy-3-phenyl-7-propyldibenzofuran

A solution of 0.97 g (0.30 mmol) of the product of Example 9 and 50 mg of 5% Pd/C in 10 mL of ethyl acetate was shaken under 40 psi H2 for 1 h. The solution was filtered through Celite and the filtrate concentrated to a colorless oil that solidified on standing at room temperature to give 0.94 (98%) of white solid.

$^1$H NMR (300 MHz, CD$_3$CN, ppm): 0.91 (t, J=7 Hz, 3H), 1.5–1.75 (m, 4H), 1.86 (m, 1H), 2.10 (m, 1H), 2.28 (d, J=3.5 Hz, 2H), 2.54 (t, J=6 Hz, 2H), 3.09 (ddd, J=10, 7, 6 Hz, 1H), 4.68 (ddt, J=6, 3.5, 1 Hz, 1H), 6.46 (sb, 1H), 6.56 (AB, dd, J=8.5, 2.5 Hz, 1H), 6.65 (AB, d, J=8.5 Hz, 1H), 6.74 (d, J=2.5 Hz, 1H), 7.25 (m, 1H), 7.36 (m, 2H), 7.54 (m, 2H);
M.S. (FAB, M+H): 307.

EXAMPLE 11

(4aS*,9bS*,3S*)-3-Butyl-3,8-dihydroxy-1,2,3,4,4a,9b-hexahydro-7-propyldibenzofuran A solution of 0.40 g (1.65 mmol) of the product of Example 2, Step A in dry tetrahydrofuran was cooled to −60° C. Then 1.4 mL of a 2.5M solution of n-butyllithium in hexane was added and the solution was stirred at −60° C. for 2 h. The reaction was quenched with 2M HCl and the mixture was partitioned between ether and water. The aqueous layer was extracted three times with ether and the combined extracts were washed with brine, dried over MgSO4, and concentrated to afford 0.348 g (71%) of a white solid.

$^1$H NMR (200 MHz, CDCl$_3$, ppm): 0.91 (t, J=Hz, 6H), 1.2–1.95 (m, 13 H), 2.15 (m, 1H), 2.54 (dd, J=6 Hz, 2H), 2.71 (s, 1H), 3.0 (q, J=6 Hz, 1H), 4.43 (s, 1H), 4.75 (m, 1H), 6.6 (s, 1H), 6.7 (s, 1H);
M.S. (FAB, M+H): 304.

EXAMPLE 12

(4aR*,9bS*)-1,2,3,4,4a,9b-Hexahydro-3-oxo-8-hydroxy-7-(2-propenyl)dibenzofuran

Step A:
(2S*,3S*)-2-Hydroxy-3-(3,5-dioxahexyl)-5-(2-propenyloxy)-2,3-dihydrobenzofuran A solution of 6.80 g (51.1 mmole) of 4-(methoxymethyloxy)butanal, 5.10 g, (60 mmole) of piperidine and 0.5 g (2.9 mmole) of p-toluene-sulfonic acid in 200 mL of benzene was heated at reflux in a 500 mL flask that had been fitted with a Dean-Stark condenser. After 4 h the solution was cooled and concentrated under reduced pressure. The residue was dissolved in 50 mL of benzene and the solution was added dropwise to 500 mL flask containing a rapidly stirring solution of 5.40 g (50 mmole) of freshly sublimed benzoquinone in 50 mL of benzene. The solution grew hot during the addition and a red precipitate formed. After 4 h the solids were dissolved by the addition of 100 mL of dry THF. The solution was cooled to 0° C. in an ice bath and to the solution were added 11.2 g (100 mmole) of potassium t-butoxide and 5.4 mL (75 mmole) of allyl bromide. The mixture was stirred for 48 h, until alkylation was complete. The reaction mixture was partitioned between ether and water and the ether layer was washed with saturated NaHCO₃ solution and saturated NaCl solution. The aqueous layers were washed sequentially with ether and the combined extracts were dried over magnesium sulfate and concentrated. The residue was purified by flash chromatography (12 cm column) using 20% ethyl acetate/hexane to afford 6.73 g (48%) of a pale orange oil. All attempts to distill this product and subsequent intermediates resulted in thermally induced Claisen rearrangement to the o-allyl phenols.

$^1$H NMR (200 MHz, CDCl₃, ppm): 1.92 (dt, J=4.5 Hz, 2H), 3.18 (m, 0.67H, trans-H3), 3.31 (s, 1H, cis-OCH3), 3.42 (s, 2H, trans-OCH3), 3.49 (m, 0.33H, cis-H3), 3.57 (t, J=6.5 Hz, 2H), 4.44 (dt, J=5.5, 1.5 Hz, 2H), 5.31 (dq, J=10.5, 1.5 Hz, 1H), 5.37 (dq, J=17, 1.5 Hz, 1H), 5.70 (d, J=2 Hz, 0.67H, trans-H2), 5.89 (d, J=6 Hz, 0.33H, cis-H2), 6.02 (ddt, J=17, 10.5, 5.5 Hz, 1H), 6.71 (m, 2H), 6.80 (m, 1H);

M.S. (m/e): 280 (5, M+), 218 (16), 177 (66), 149 (12), 98 (100), 84 (22), 73 (64), 55 (16).

Step B: Methyl (2R*,3S*)-[3-(3,5-dioxahexyl)-2,3-dihydro-5-(2-propenyloxy)-2-benzofuranyl]acetate A solution of 18.5 g (66.0 mmole) of the product of Example 12, Step A and 25.0 g (74.8 mmole) of methyl (triphenylphosphoranylidene)acetate in 100 mL of THF was heated at reflux for 4 h. Then 100 mL of methanol and 5 mL (52 mmole) of piperidine were added and heating was continued for 2 h. The solution was concentrated and the residue was dissolved in ether. The solids were removed by filtration and the filtrate was concentrated and purified by flash chromatography (10 cm column) using 25% ethyl acetate-hexane to afford 19.0 g (86%) of a pale orange oil identical to that prepared by the two step procedure.

$^1$H NMR (200 MHz, CDCl₃, ppm): 1.96 (dt, J=6.5, 3.5 Hz, 1H), 1.99 (dt, J=6.5, 2 Hz, 1H), 2.66 (AB, dd, J=16, 5.5 Hz, 1H), 2.75 (AB, dd, J=16, 8 Hz, 1H), 3.23 (dt, J=7, 5.5 Hz, 1H), 3.38 (s, 3H), 3.69 (t, J=6.5 Hz, 2H), 3.72 (s, 3H), 3.73 (s, 0.06H, cis isomer), 4.45 (dt, J=5.5, 1.5 Hz, 2H), 4.86 (dt, J=7.5, 5.5 Hz, 1H), 5.27 (dq, J=10.5, 1.5 Hz, 1H), 5.37 (dq, J=17, 1.5 Hz, 1H), 6.03 (ddt, J=17, 10.5, 1.5 Hz), 6.66 (m, 2H), 6.77 (m, 1H);

M.S. (m/e): 336 (100, M+), 273 (28), 263 (42), 189 (24), 177 (64), 161 (28), 147 (18), 91 (12), 59 (10), 55 (10).

Step C: Methyl (2R*,3S*)-[3-(2-hydroxyethyl)-2,3-dihydro-5-(2-propenyloxy)-2-benzofuranyl]acetate A solution of 18.0 g (53.5 mmole) of the product of Example 12, Step B in 100 mL of dry methanol was cooled to 0° C. in an ice bath. Then 10 mL (89 mmole) of BF₃-etherate was added and the solution was stirred at room temperature for 48 h. The solution was neutralized by the addition of saturated NaHCO₃ solution and the mixture was partitioned between ether and saturated NaHCO₃ solution. The aqueous layers were sequentially washed with ether and the combined ether extracts were dried over magnesium sulfate and concentrated. The residue was purified by flash chromatography (10 cm column) using 30% ethyl acetate/hexane to afford 14.6 g (93%) of a pale yellow oil.

$^1$H NMR (200 MHz, CDCl₃, ppm): 1.81 (AB, ddt, J=14, 8.5, 5.5 Hz, H), 1.92 (ddt, J=14, 5.5, 5 Hz, 1H), 2.08 (sb, 1H), 2.73 (AB, dd, J=16, 7 Hz, 1H), 2.82 (AB, dd, J=15, 7 Hz, 1H), 3.33 (ddd, J=4.5, 5.5, 8.5 Hz, 1H), 3.77 (s, 3H), 3.85 (dt, J=6, 5.5 Hz, 2H), 4.51 (ddd, J=5.5, 1.5, 1 Hz, 2H), 4.96 (dt, J=7, 4.5 Hz, 1H), 5.27 (ddt, J=10.5, 1.5, 1 Hz, 1H), 5.38 (ddt, J=17, 1.5, 1 Hz, 1H), 6.03 (ddt, J=17, 10.5, 5.5 Hz, 1H), 6.69 (m, 2H), 6.78 (m, 1H);

M.S. (m/e): 292 (26, M+), 219 (22), 177 (100), 149 (20), 91 (14), 77 (10), 55 (12).

Step D: Methyl (2R*,3S*)-[3-(2-chloroethyl)-2,3-dihydro-5-(2-propenyloxy)-2-benzofuranyl]acetate A mixture of 14.4 g (49.2 mmole) of the product Example 12, Step C and 20.0 g (76.0 mmole) of triphenylphosphine in 20 mL of acetonitrile was stirred at room temperature until the solid dissolved. Then 10 mL of carbon tetrachloride was added and the solution was stirred without external cooling for 4 h, until conversion was complete by tlc (30% ethyl acetate-hexane). The solution was concentrated and the residue was purified by flash chromatography to afford 13.4 g (87%) of a pale yellow oil.

$^1$H NMR (200 MHz, CDCl₃, ppm): 2.12 (dt, J=7, 5 Hz, 2H), 2.63 (AB, dd, J=16, 6.5 Hz, 1H), 2.78 (AB, dd, J=16, 7.5 Hz, 1H), 3.33 (dt, J=7, 5 Hz, 1H), 3.78 (s, 3H), 3.69 (dt, J=7, 5 Hz, 2H), 4.52 (ddd, J=5, 2, 1.5 Hz, 2H), 4.89 (ddd, J=7, 6, 5.5 Hz, 1H), 5.28 (ddt, J=11.5, 2, 1.5 Hz, 1H), 5.37 (ddt, J=17, 2, 1.5 Hz, 1H), 6.04 (ddt, J=17, 11.5, 5.5 Hz, 1H), 6.70 (m, 2H), 6.80 (m, 1H);

M.S. (m/e): 312 (22, M+), 310 (68, M+), 271 (32), 269 (100), 239 (8), 237 (28), 211 (16), 209 (50), 175 (8), 173 (38), 147 (20), 117 (18), 91 (18), 77 (16), 55 (16).

Step E: (2R*,3S*)-[3-(2-Chloroethyl)-2,3-dihydro-5-(2-propenyloxy)-2-benzofuranyl]ethanal A solution of 13.3 g (42.7 mmole) of the product of Example 12, Step D in 200 mL of toluene was cooled to −78° C. in a dry ice-isopropanol bath. The 30 mL (45 mmole) of a 1.5M solution of DIBAL-H in toluene was added dropwise and the solution was stirred at −78° C. for 2 h, until reduction was complete. Excess hydride was destroyed by the addition of 10 mL of a 2M methanolic HCl solution and solution was partitioned between ether and 0.2M HCl. The aqueous layer was washed with ether and the ether extracts were washed sequentially with water and saturated NaCl solution. The combined extracts were dried over magnesium sulfate and concentrated to afford 11.9 g (98%) of a colorless oil. This material was not purified but used directly in the next step.

$^1$H NMR (200 MHz, CDCl₃, ppm): 2.12 (dt, J=7, 6.5 Hz, 2H), 2.74 (AB, ddd, J=17, 5.5, 1.5 Hz, 1H), 2.89 (AB, ddd, J=17, 7.5, 2 Hz, 1H), 3.29 (dt, J=7, 4 Hz, 1H), 3.71 (t, J=6.5 Hz, 2H), 4.45 (ddt, J=5, 2, 1.5 Hz, 2H), 4.91 (ddd, J=7.5, 5.5, 4 Hz, 1H), 5.27 (ddt, J=10.5, 2, 1.5 Hz, 1H), 5.38 (ddt, J=17, 2, 1.5 Hz, 1H), 6.03 (ddt, J=17, 10.5, 5.5 Hz, 1H), 6.71 (m, 2H), 6.81 (m, 1H), 9.84 (dd, J=2, 1.5 Hz);

M.S. (m/e): 282 (14), 280 (48), 241 (30), 280 (50), 241 (32), 239 (100), 177 (34), 157 (28), 147 (52), 119 (32), 105 (34), 91 (76), 77 (60), 65 (50), 55 (86).

Step F:
(2R*,3S*)-3-[3-(2-Chloroethyl)-2,3-dihydro-5-(2-propenyloxy)-2-benzofuranyl-2-trimethylsilyloxy]-propanonitrile A solution of 11.9 g (42.2 mmole) of the product of Example 12, Step E and 0.500 g (8.77 mmole) KCN in 25 mL of cyanotrimethylsilane was stirred at 20° C. for 24 h until the tlc (25% ethyl acetate-hexane) indicated that conversion to the cyanohydrin was complete. The excess cyanotrimethylsilane was removed by distillation under high vacuum and the residue was taken up in dichloromethane and filtered. The filtrate was concentrated and dried under high vacuum to afford 16.4 g (94%) of a pale yellow oil.

$^1$H NMR (200 MHz, CDCl$_3$, ppm): 0.20 (s, 9H), 1.9–2.1 (m, 4H), 3.38 (dt, J=7, 4 Hz, 1H), 3.65 (t, J=6.5 Hz, 2H), 4.45 (dq, J=5.5, 1.5 Hz), 4.72 (dt, J=6, 2 Hz, 1H), 4.96 (ddd, J=7.5, 5.5, 4 Hz, 1H), 5.27 (dq, J=10.5, 1.5 Hz, 1H), 5.38 (dq, J=17, 1.5 Hz, 1H), 6.03 (ddt, J=17, 10.5, 5.5 Hz, 1H), 6.71 (m, 2H), 6.81 (m, 1H);

M.S. (m/e): 381 (0.2, M+), 379 (0.8, M+), 309 (22), 307 (70), 268 (27), 266 (100), 239 (42), 197 (32), 195 (30), 161 (22), 147 (28), 119 (14), 92 (28), 77 (22), 55 (34).

Step G:
(3R*,3S*)-3-[3-(2-Chloroethyl)-2,3-dihydro-5-(2-propenyloxy)-2-benzofuranyl-2-(1-ethoxyethyloxy)]-propanonitrile A solution of 4.12 g (10.0 mmole) of the product of Example 12, Step F in 20 mL of THF was cooled to 0° C. in an ice bath. Then 10 mL of a 1M solution of tetrabutylammonium fluoride in THF was added dropwise over 5 minutes; after addition was complete, 6 mL of trifluoroacetic acid was added and solution was stirred at 0° C. for 30 min. Then 5 mL of ethyl vinyl ether and 0.5 mL of trifluoroacetic acid were added and the solution was stirred at room temperature for 6 h, until reaction was complete. Two product spots (diastereomers) could be seen by tlc (10% ethyl acetate-hexane). The solution was partitioned between ether and saturated NaHCO$_3$ solution and the aqueous layer was washed with ether. The ether extracts were sequentially washed with saturated NaHCO$_3$ solution, then saturated NaCl solution. The combined extracts were dried over magnesium sulfate and concentrated and the residue was purified by flash chromatography (5 cm column) using 10% ethyl acetate-hexane to afford 2.97 g (78%) of a colorless oil that was a mixture of diastereomers.

$^1$H NMR (200 MHz, CDCl$_3$, ppm): 1.21, 1.24 (t, J=7.0 Hz, total 3H), 1.32, 1.34 (d, J=5.5 Hz, total 3H), 2.02–2.23 (m, 4H), 3.15–3.40 (m, 1H), 3.65 (t, J=6.5 Hz, 2H), 3.50–3.80 (m, 2H), 4.45 (dq, J=5.5, 1.5 Hz), 4.60 (m, 1H), 4.80 (m, 1H), 4.90–5.10 (m, 1H), 5.28 (dq, J=10.5, 1.5 Hz, 1H), 5.39 (dq, J=17, 1.5 Hz, 1H), 6.04 (ddt, J=17, 10.5, 5.5 Hz, 1H), 6.70 (m, 2H), 6.80 (m, 1H);

M.S. (m/e): 380 (0.8, M+H), 378 (3, M+H), 309 (12), 307 (40), 241 (16), 239 (52), 197 (36), 195 (34), 161 (26), 147 (44), 119 (22), 91 (50), 77 (44), 65 (46), 55 (100).

Step H:
(4aR*,9bS*)-3-Cyano-3-(1-ethoxyethoxy)-1,2,3,4,4a,9b-tetrahydro-8-(2-propenyloxy)dibenzofuran A solution of 10.0 g (26.3 mmole) of the product of Example 12, Step G in 75 mL of THF was cooled to 0° C. in an ice bath. To this was added 40 mL of 1M solution of sodium hexamethyldisilazide in THF and the solution was heated at 60° C. for 1 h. A precipitate formed immediately upon addition of the base and tlc (10% ethyl acetate-hexane) indicated the formation of two products that moved slightly faster than the starting mixture. The mixture was partitioned between ether and water and the aqueous layer was washed with ether; then the ether extracts were sequentially washed with saturated NaHCO$_3$ solution and saturated NaCl solution. The combined extracts were dried over magnesium sulfate and concentrated and the residue was purified by flash chromatography to afford 8.14 g (90%) of a white crystalline powder.

MP 87°–95° C.;

$^1$H NMR (300 MHz, CD$_3$CN, ppm): 1.151, 1.153, 1.17 (t, J=7.0 Hz, total 3H), 1.304, 1.312, 1.34 (d, J=5.5 Hz, total 3H), 1.6–2.0 (m, 2H), 2.2–2.5 (m, 2H), 2.8–3.0 (m, 3H), 3.40–3.75 (m, 2H), 3.98, 4.07 (ddd, J=12.6, 12.4, 3.6 Hz, total 1H), 4.47 (dq, J=5.5, 1.5 Hz), 5.11, 5.13 (dq, J=5.5 Hz, total 1H), 5.28 (dq, J=10.5, 1.5 Hz, 1H), 5.39 (dq, J=17, 1.5 Hz, 1H), 6.04 (ddt, J=17, 10.5, 5.5 Hz, 1H), 6.65–6.73 (m, 2H), 6.82 (m, 1H);

M.S. (m/e): 343 (18, M+), 271 (12), 244 (22), 203 (38), 185 (32), 147 (12), 91 (14), 73 (100), 55 (22).

Step I:
(4aR*,9bS*)-1,2,3,4,4a,9b-Hexahydro-3-oxo-8-hydroxy-7-(2-propenyl)dibenzofuran A solution of 1.52 g (4.42 mmol) of the product of Example 12, Step H in 20 mL of CH$_2$Cl$_2$ was cooled to 0° C. under nitrogen. Then 5 mL of a 1.0M BCl$_3$ solution was added and the solution was stirred at 0° C. for 30 min. The reaction was quenched by addition of 10 mL of saturated NaHCO$_3$ solution and the mixture was partitioned between ether and water. The organic extract was washed with saturated NaHCO$_3$ solution and brine, dried over MgSO$_4$, and concentrated. The residue was purified by flash chromatography on silica gel using 30% ethyl acetate-hexane and that material crystallized from ether to afford 0.420 g (40%) of white crystal.

$^1$H NMR (300 MHz, CD$_3$CN, ppm): 1.70 (m, 1H), 2.10 (m, 1H), 2.23–2.40 (m, 3H), 2.65–2.95 (m, 2H), 3.4 (m, 2H), 4.08 (dt, J=12.5, 4.0 Hz), 5.20 (m, 3H), 6.64 (s, 1H), 6.80 (s, 1H), 7.68 (s, b, 1H); M.S. (FAB, M+H): 245.

EXAMPLE 13

(4aR*,9bS*)-1,2,3,4,4a,9b-Hexahydro-3-oxo-8-hydroxy-7-propyldibenzofuran

A suspension of 0.250 g (1.02 mmol) of the product of Example 12, Step I and 50 mg of 5% Pd/C in 5 mL of ethyl acetate was shaken under 40 psi H$_2$ for 1 h. The solution was filtered through Celite and the filtrate was concentrated to afford 0.250 g (100%) of a white powder.

$^1$H NMR (300 MHz, CD$_3$CN, ppm): 0.91 (t, J=7 Hz, 1H), 1.70 (m, 1H), 1.54 (m, 2H), 2.10 (m, 1H), 2.23–2.40 (m, 3H), 2.53 (t, J=6 Hz, 2H), 2.65–2.95 (m, 2H), 4.08 (dt, J=12.5, 4.0 Hz), 6.64 (s, 1H), 6.80 (s, 1H), 7.68 (s, b, 1H);

M.S. (FAB, M+H) 247.

EXAMPLE 14

(4aR*,b 9bS*)-1,2,3,4,4a,9b-Hexahydro-3-oxo-8-hydroxy-dibenzofuran

Step A:
(4aR*,9bS*)-3-Cyano-3-hydroxy-1,2,3,4,4a,9b-tetrahydro-8-hydroxy-dibenzofuran A solution of 0.500 g (1.40 mmole) of the product of Example 12, Step G and 0.020 g (0.110 mmole) of p-toluenesulfonic acid in 5 mL of benzene and 2 mL of methanol was heated at reflux for 6 h. The solution was partitioned between ethyl acetate-saturated NaCl solution and the ethyl acetate layer was dried over magnesium sulfate and concentrated. The residue was purified by flash chromatography (2 cm column) using 30% ethyl acetate-hexane and crystallized from ethyl acetate hexane to afford 0.181 g (56%) of colorless needles,
MP 246°-247° C.;

$^1$H NMR (300 MHz, CD$_3$CN, ppm): 1.65-1.90 (m, 1H), 2.05 (m, 1H), 2.20-2.40 (m, 3H), 2.75-3.05 (m, 2H), 4.11 (dt, J=12.5, 4.0 Hz), 5.66 (s, b, 1H), 6.65 (m, 2H), 6.80 (m, 1H), 7.66 (s, b, 1H);

M.S. (m/e): 231 (100, M+), 204 (98), 186 (24), 161 (50), 149 (76), 147 (84), 123 (72), 121 (18), 103 (12), 91 (22), 81 (14), 77 (24), 65 (20), 55 (50).

Step B:
(4aR*,9bS*)-1,2,3,4,4a,9b-Hexahydro-3-oxo-8-hydroxy-dibenzofuran

A solution of 0.025 g (0.108 mmol) of the product of Example 14, Step A in 1 mL of dimethylsulfoxide was heated at 45° C. under 0.1 mm vacuum for 20 min. The solution was concentrated under vacuum and the residue was crystallized by addition of ether to afford 0.014 g (63%) of white crystals.
MP 199°-201° C.;

$^1$H NMR (300 MHz, CD$_3$CN, ppm): 1.70 (m, 1H), 2.10 (m, 1H), 2.23-2.40 (m, 3H), 2.65-2.95 (m, 2H), 4.08 (dt, J=12.5, 4.0 Hz), 6.64 (m, 2H), 6.80 (m, 1H), 7.68 (s, b, 1H);

M.S. (m/e): 204 (100, M+), 161 (56), 149 (80), 123 (78), 91 (24), 77 (28), 65 (24), 55 (56).

EXAMPLE 15

(4aR*,9bS*)-3,8-Dihydroxy-1,2,3,4,4a,9b-hexahydro-7-propyldibenzofuran

The reduction of the product of Example 12 can be accomplished following the procedure of Example 6.

EXAMPLE 16

(4aR*,9bS*)-3,8-Dihydroxy-1,2,3,4,4a,9b-hexahydro-3-phenyl-7-prop-2-enyldibenzofuran The addition of phenyl magnesium chloride to the product of Example 12 can be accomplished following the procedure of Example 9.

EXAMPLE 17

(4aR*,9bS*)-3,8-Dihydroxy-1,2,3,4,4a,9b-hexahydro-3-phenyl-7-propyldibenzofuran

The reduction of the product of Example 16 can be accomplished following the procedure of Example 6.

What is claimed is:

1. A compound of Formula I wherein:

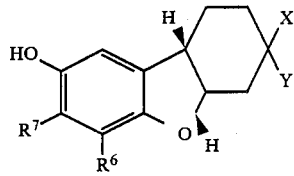

I $R^6$ is:
(C$_1$-C$_6$)-straight or branched chain alkyl or (C$_2$-C$_6$)-alkenyl; and
hydrogen, when $R^7$ is not hydrogen;

$R^7$ is:
hydrogen,
(C$_1$-C$_6$)-straight or branched chain alkyl or (C$_2$-C$_6$)-alkenyl; and X and Y together are a keto group, or
X and Y are different and are independently H, OH, (C$_1$-C$_6$)-alkyl, or phenyl, except that if X or Y is (C$_1$-C$_6$)-alkyl, then Y or X cannot be phenyl,
or pharmaceutically acceptable salts thereof.

2. A compound of Formula II wherein:

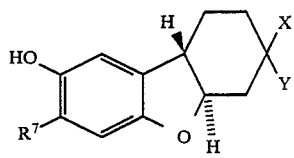

II $R^7$ is:
(C$_1$-C$_6$)-straight or branched chain alkyl or (C$_2$-C$_6$)-alkenyl; and
X and Y together are a keto group, or
X and Y are different and are independently H, OH, (C$_1$-C$_6$)-alkyl, or phenyl, except that if X or Y is (C$_1$-C$_6$)-alkyl, then Y or X cannot be phenyl,
or pharmaceutically acceptable salts thereof.

3. A compound of claim 1 wherein the groups of Formula I are:
$R^6$ is:
hydrogen, when $R^7$ is not hydrogen,
1-prop-2-enyl, when $R^7$ is hydrogen,
n-propyl, when $R^7$ is hydrogen;
$R^7$ is:
hydrogen,
1-prop-2-enyl, when $R^6$ is hydrogen, or
n-propyl, when $R^6$ is hydrogen; and
X and Y together are a keto group, or
X and Y are different, and are independently H, OH, (C$_1$-C$_6$)-alkyl, or phenyl, except that if X or Y is (C$_1$-C$_6$)-alkyl, then Y or X cannot be phenyl,
or pharmaceutically acceptable salts thereof.

4. A compound of Formula II, according to claim 2, where the selected groups are:
$R^7$ is:
1-prop-2-enyl, or
n-propyl; and
X and Y together are a keto group.

5. A compound of claim 1 which is
(4aS*,9bS*)-1,2,3,4,4a,9b-hexahydro-8-hydroxy-7-methyldibenzofuran-3-one;
(4aS*,9bS*)-1,2,3,4,4a,9b-hexahydro-8-hydroxy-6-propyldibenzofuran-3-one;
(4aS*,9bS*)-1,2,3,4,4a,9b-hexahydro-8-hydroxy-7-propyldibenzofuran-3-one;

(4aR*,9bS*)-1,2,3,4,4a,9b-hexahydro-8-hydroxy-7-prop-2-enyldibenzofuran-3-one; (4aR*,9bS*)-1,2,3,4,4a,9b-hexahydro-8-hydroxy-7-propyldibenzofuran-3-one (4aS*,9bS*,3R*)-3,8-dihydroxy-1,2,3,4,4a,9b-hexahydro-3-phenyl-7-propyldibenzofuran;

(4aS*,9bS*,3R*)-3-n-butyl-3,8-dihydroxy-1,2,3,4,4a,9b-hexahydro-7-propyldibenzofuran;

(4aS*,9bS*,3R*)-3,8-dihydroxy-1,2,3,4,4a,9b-hexahydro-7-propyldibenzofuran;

(4aS*,9bS*,3S*)-3,8-dihydroxy-1,2,3,4,4a,9b-hexahydro-7-prop-2-enyldibenzofuran;

(4aS*,9bS*,3S*)-3,8-dihydroxy-1,2,3,4,4a,9b-hexahydro-7-propyldibenzofuran;

(4aS*,9bS*,3R*)-1,2,3,4,4a,9b-hexahydro-8-hydroxy-3-phenyl-7-propyldibenzofuran;

(4aR*,9bS*,3S*)-3,8-dihydroxy-1,2,3,4,4a,9b-hexahydro-7-prop-2enyldibenzofuran; or (4aR*,9bS*)-3,8-dihydroxy-1,2,3,4,4a,9b-hexahydro-3-phenyl-7-prop-2-enyldibenzofuran;

or pharmaceutically acceptable salts thereof.

6. A method of inhibiting mammalian leukotriene biosynthesis or action which comprises administering to a mammal a pharmaceutically effective amount of a compound of claim 1.

7. A method of inhibiting mammalian leukotriene biosynthesis or action which comprises administering to a mammal a pharmaceutically effective amount of a compound of claim 2.

8. A method of claim 6 wherein the mammal is a human.

9. A method of claim 7 wherein the mammal is a human.

10. A method of treating pulmonary conditions, inflammation, cardiovascular conditions or skin conditions which comprises administering to a human in need of such treatment a pharmaceutically effective amount of a compound of claim 1.

11. A method of treating pulmonary conditions, inflammation, cardiovascular conditions or skin conditions which comprises administering to a human in need of such treatment a pharmaceutically effective amount of a compound of claim 2.

* * * * *